United States Patent [19]
Affleck et al.

[11] Patent Number: 5,827,663
[45] Date of Patent: Oct. 27, 1998

[54] METHOD AND APPARATUS FOR REDUCING SOLVENT LUMINESCENCE BACKGROUND EMISSIONS

[75] Inventors: Rhett L. Affleck; W. Patrick Ambrose, both of Los Alamos, N. Mex.; James N. Demas, Charlottesville, Va.; Peter M. Goodwin, Jemez Springs, N. Mex.; Mitchell E. Johnson, Pittsburgh, Pa.; Richard A. Keller; Jeffrey T. Petty, both of Los Alamos, N. Mex.; Jay A. Schecker, Santa Fe, N. Mex.; Ming Wu, Los Alamos, N. Mex.

[73] Assignee: The Regents of the University of California, Los Alamos, N. Mex.

[21] Appl. No.: 727,841

[22] Filed: Oct. 4, 1996

Related U.S. Application Data

[63] Continuation of Ser. No. 383,272, Feb. 3, 1995, abandoned.
[51] Int. Cl.[6] ............................. C12Q 1/68; C12Q 1/37; C12N 15/00
[52] U.S. Cl. .................... 435/6; 435/23; 935/77
[58] Field of Search .................. 435/6, 23, 24, 435/808, 968; 422/82.08; 935/77

[56] References Cited

U.S. PATENT DOCUMENTS

| | | | |
|---|---|---|---|
| 4,793,705 | 12/1988 | Shera | 356/318 |
| 4,962,037 | 10/1990 | Jett et al. | 435/6 |
| 5,215,883 | 6/1993 | Chu | 435/6 |
| 5,424,186 | 6/1995 | Fodor et al. | 435/6 |

OTHER PUBLICATIONS

Jong Hoon Hahn et al., "Laser–Induced Fluorescence Detection of Rhodamine–6G at 6 x $10^{15}$ M," 45 Applied Spectroscopy, No. 5, pp. 743–746 (1991).

J. C. White et al., "Photostability Studies of Phycobiliprotein Fluorescent Labels," 161 Analytical Biochemistry, pp. 442–452 (1987).

Steven A. Soper et al., "The Photophysical Constants of Several Fluorescent Dyes Pertaining to Ultrasensitive Fluorescence Spectroscopy," 57 Photochemistry and Photobiology, No. 6, pp. 972–977 (1993).

Peter M. Goodwin et al., "Ultrasensitive Detection of Single Molecules in Flowing Sample Streams By Laser–Induced Fluorescence," 1895 SPIE Ultrasensitive Laboratory Diagnostics, pp. 79–89 (1993).

E. Brooks Shera et al., "Detection of Single Fluorescent Molecules,"174 Chemical Physics Letters No. 6, pp. 553–557 (1990).

Goodwin, P., DNA Sequencing by Single Molecule Detection of Labeled Nucleotides Sequentially Cl Cleaved From a Single Strand of DNA, SPIE vol. 1891 (1993) pp. 127–131.

Ambrose, W., Single Molecule Detection and Photochemistry on a Surface Using Near–Field Optical Excitation, Physical Review Letters, vol. 72, No. 1, (1994) pp. 160–163.

*Primary Examiner*—Ralph Gitomer
*Attorney, Agent, or Firm*—Ray G. Wilson

[57] ABSTRACT

The detectability of luminescent molecules in solution is enhanced by reducing the background luminescence due to impurity species also present in the solution. A light source that illuminates the solution acts to photolyze the impurities so that the impurities do not luminesce in the fluorescence band of the molecule of interest. Molecules of interest may be carried through the photolysis region in the solution or may be introduced into the solution after the photolysis region.

14 Claims, 4 Drawing Sheets

METHOD AND APPARATUS FOR REDUCING SOLVENT LUMINESCENCE BACKGROUND EMISSIONS

This is a continuation of application Ser. No. 08/383,272 filed on Feb. 3, 1995 now abandoned.

This invention was made with government support under Contract No. W-7405-ENG-36 awarded by the U.S. Department of Energy. The government has certain rights in the invention.

BACKGROUND OF THE INVENTION

This invention relates to luminescence detection, and, more particularly, to sensitive luminescence detection in flowing sample streams.

Laser-induced fluorescence is a sensitive tool for chemical and biological analysis. One major attribute associated with the widespread applicability of fluorescence spectroscopy is the low limits of detection that are attainable, especially when a laser is used as the excitation source. For example, single molecules of Rhodamine 6G have been detected by exciting the molecules with a mode-locked laser that allowed the use of a time-gate to discriminate promptly scattered photons from delayed or fluorescence photons. See E. B. Shera et al., "Detection of Single Fluorescent Molecules," 174 Chem. Phys. Lett., No. 6, 553 (1990), incorporated herein by reference.

Sensitive fluorescence detection in solution is limited by the noise associated with background emission and scattering from the solvent. This is particularly acute when several different fluorescent molecules are being presented to the fluorescence detection system, such as, e.g., rapid base sequencing in DNA and RNA, described in James H. Jett et al., U.S. Pat. No. 4,962,037, issued Oct. 9, 1990, and incorporated herein by reference. There have been many attempts to provide a distinguishable signal: increase the number of photons emitted by a fluorescent molecule, gated detection techniques, limited probe volume, and others.

Some applications may permit the use of an ultrapure solvent, e.g., ultrapure water; in attempt to reduce the background photon counts from impurities in the solvent but even ultrapure solvents contain some trace impurities. In many biological systems, a buffer is a required additive to maintain pH levels suitable to the biological particles being examined. If nucleotides are to be cleaved from DNA, as described in the '037 patent, an exonuclease must be included in the solvent. Each of these additives potentially further increases the photon count from "impurities" in the solvent.

Accordingly, it is an object of the present invention to greatly reduce, or eliminate, background fluorescence from impurities present in a probe volume of a luminescence detection system.

It is another object of the present invention to reduce impurity fluorescence in the probe volume of a luminescence detection system while maintaining the efficacy of active components in the solvent.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, this invention may comprise a method for removing background luminescence in a detection system for light-excited luminescence from a sample carried in a solvent. The solvent is photobleached with a selected agent, e.g., light, in a first region of the detection system. The solvent is introduced into a second region of the detection system that is downstream of the first region, wherein the selected agent is absent from the second region. The sample is then excited with light that has a wavelength effective to luminesce the sample in an excitation volume of the second region. The sample may be carried with the solvent through the first region or may be introduced into the solvent downstream of the first region.

In another characterization, an improved solvent delivery system is provided in a system for detecting light-excited luminescence from a sample carried by a solvent. A first region is provided for photobleaching the solvent with a selected agent. A second region is connected to receive the solvent from the first region and is free of the selected agent. A luminescence detection system is connected to the second region for exciting the sample with a wavelength effective to excite the sample to luminescence.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Figure 1:
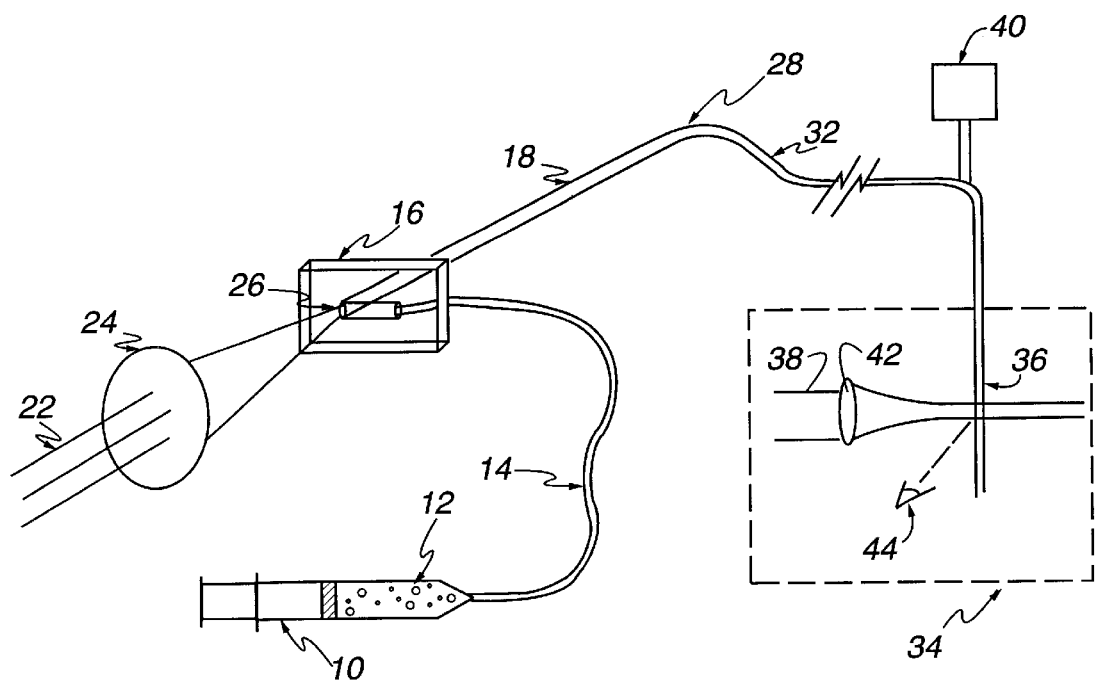
FIG. 1 a pictorial illustration of a system for in-line photobleaching of a solution before delivery to a ultrasensitive luminescence detection system.

In accordance with our invention, a solvent used in a sensitive fluorescence detection system is subjected to a selected agent, e.g., light, to photobleach the solvent before a sample, whose luminescence is to be measured, is introduced into the solvent. By photobleaching, we mean any photochemical process, i.e., any photon-induced reaction, that transforms a luminescent interferent into either a non-luminescent species or a species that does not luminesce at a wavelength that interferes with a selected detected wavelength of analyte luminescence or that greatly reduces the luminescence quantum yield at the wavelength from analyte luminescence. Likewise, the use of the term "solvent" may include a solvent alone or a solution of the solvent with solutes, such as the sample, or other constituents, such as a reactant that forms luminescent products with the analyte, unless otherwise specified.

Photobleaching, also photodestruction, is a process that alters a molecule, so that subsequent exposure to an otherwise exciting light wavelength does not induce luminescence. See J. C. White et al., "Photostability Studies of Phycobiliprotein Fluorescent Labels," 161 Anal. Biochemistry, 442 (1987), for a theoretical discussion. Thus, for a solvent that is optically dilute at the photolysis wavelength, and for uniform illumination of the solvent, it can be shown that the amount of impurity molecules that survive photobleaching is given by:

$$f_{survive} = \exp[-2303 P_0 \epsilon \phi_d (L/V)],$$

where $f_{survive}$ is the sample fraction that survives photobleaching; $P_0$ is the incident intensity of light in ein/cm$^2$s (where an einstein (ein) of light is 1 mole of photons or $6.023 \times 10^{23}$ photons); $\epsilon$ is the molar extinction coefficient; $\phi_d$ is the quantum yield for photobleaching (moles/ein) or number of molecules photobleached/number of photons absorbed; L is the length of the flow cell (cm); and V is the volume flow rate of solvent through the flow cell (ml/s). Thus, any desired amount of attenuation for a given impurity can be obtained by selecting appropriate system parameters, i.e., light power and solvent flow rate, to approach a condition where the background impurity luminescence is greatly reduced or eliminated ($f_{survive} \rightarrow 0$)

Table A illustrate the percent fraction of luminescent molecules exiting the photolysis cell as a function of the length of the cell and the molecular parameter $\epsilon \phi_d$. Because of the exponential dependence, the efficiency of removal increases rapidly with path length and $\epsilon \phi_d$.

TABLE A

Effect of Photolysis Parameters on Success of Photobleaching of Impurities[a]
Fraction of Molecules Surviving a Photolysis Path of

| $\epsilon \phi_d$ | 1 cm | 10 cm | 100 cm |
|---|---|---|---|
| 0.001 | 1.00 | 0.97 | 0.73 |
| 0.01 | 0.97 | 0.73 | 0.041 |
| 0.1 | 0.73 | 0.041 | $10^{-14}$ |
| 1.0 | 0.046 | $10^{-14}$ | 0 |

[a]Based on a photolysis power of 250 mW at 554 nm in a 0.5 mm id photolysis tube with a flow rate of $8.33 \times 10^{-4}$ mL/s It will be appreciated that the only requirement to obtain useful results according to the present invention is that solution impurities photobleach to a greater extent than a sample, e.g., a luminescent molecule, in the solution. For example, the data presented below shows that, in a solution of B-phycoerythrin and TRITC, photobleaching the solution would greatly reduce or eliminate the B-phycoerythrin fluorescence at a detector to enhance the detectability of the TRITC in the detector. The process is simplified with multiple photobleaching wavelengths, so that a spectral wavelength may be found that photolyses only the impurities, leaving the sample available to luminesce at a detector.

An exemplary system for detecting light-induced fluorescence according to the present invention is shown in FIG. 1. Fluid injection system 10, which may be a controlled pump or a syringe or the like, causes a solvent 12 to flow through inlet tubing 14 to input coupling cell 16. Solvent 12 is passed through input coupling cell 16 to photolysis cell 18, which may be a length of tubing that is sufficient to meet the functional requirements discussed above for photobleaching of the solvent.

Photolysis light source 22, which may be a laser or other light having a wavelength effective to photobleach solvent 12, is focused by focusing system 24 to form focused light 26 into solvent 12 within photolysis cell 18. Requirements for focusing system 24 are further discussed with reference to FIG. 2. Focusing devices, such as lens and the like, are well known for laser and other light sources, and are not described in detail herein. Photolysis cell 18 is provided with a mechanism to remove the photolysis agent, such as focused light beam 26 from photolysis cell 28. If the photolysis agent is a light, photolysis cell 18 may simply be provided with a surface having an angle that transmits, rather than reflects, the focused light beam 26 to remove the light from photolysis cell 28.

Photobleached solvent is then delivered to detection system 34 through connecting tubing 32. A sample to be detected by detection system 34 is introduced into solvent 12 only after the solvent is photobleached. The sample may be injected into solvent 12 by injection system 40, which may be a syringe, pump, or other suitable fluid moving device, or the sample may be suspended in the solvent, as described in U.S. Pat. No. 4,962,037.

The sample is then delivered in photobleached solvent 12 to detection system 34. The sample is then excited by excitation beam 34, which is focused into detection cell 36 by excitation beam focusing system 42. The resulting fluorescence from the sample is detected by detector 44, which is conventionally a photomultiplier tube, avalanche diode, or other detector that detects photons emitted from an excited sample. Suitable sensitive detection devices are described by J. H. Hahn et al., "Laser-induced Fluorescence Detection of Rhodamine-6G at $6 \times 10^{-15}$M," 45 Applied Spectroscopy, No. 5, 743 (1991), or by E. B. Shera, U.S. Pat. No. 4,793,705, issued Dec. 12, 1988, and by L-Q Li et al., "Single Photon Avalanche Diode for Single Molecule Detection," 64 Rev. Sci. Instrum., 1524 (1993), both incorporated herein by reference. Solvent 12 is photobleached and is not excited by excitation beam 34 and the fluorescence presented to the detection region 36 of ultrasensitive detector 44 arises substantially from the sample being detected. The signal-to-noise ratio is greatly increased by the reduction in noise from the solvent system.

In some instances, it may be desirable to include in solvent 12 a component that interacts with the sample. For example, if a DNA strand is being sequenced, an exonuclease is required to cleave individual nucleotides from a sample, as described in the '037 patent. Also, the reaction between a reactant and the sample may be important so that a selected reactant is included in solvent 12. In some instances, the photobleaching process can be used to photobleach the included reactant without significantly reducing the desired reaction so that the reactant may be included in the solvent injected by fluid injection system 10. In yet other instances, the efficacy of the reactant is diminished and the reactant must be injected into the solvent downstream of photolysis cell 18. By downstream is meant a location that is between photolysis cell 18 and detection system 34. Injector 40 may then also include injection means for the reactant so that a suitable interaction occurs before solvent 12, an injected sample, and an injected reactant occur before the mixture reached detection cell 36.

Figure 2:
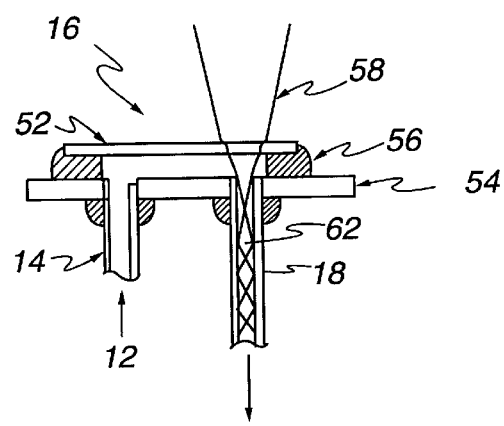
FIG. 2 is a cross-sectional view of a coupling system for introducing a light photobleaching agent into a solvent stream.

FIG. 2 more particularly depicts a cross-sectional view of coupling system 16. Photolysis inlet window 52 is spaced above substrate 54 by support 56, which also acts to seal coupling system 16. substrate 54 defines an opening for fluid inlet tube 14 and photolysis cell 18, both of which are sealingly coupled to substrate 54.

Focused photolysis beam 58 is transmitted by window 52 to within photolysis cell 18. In one embodiment, photolysis cell 18 is a tube and focusing system 24 focusing the photolysis beam an angle that maximizes internal reflection from interior surfaces of photolysis cell 18 to form internally reflecting beam 62 that is transmitted within cell 18 and solvent 12 to photobleach solvent 12.

Figure 3:
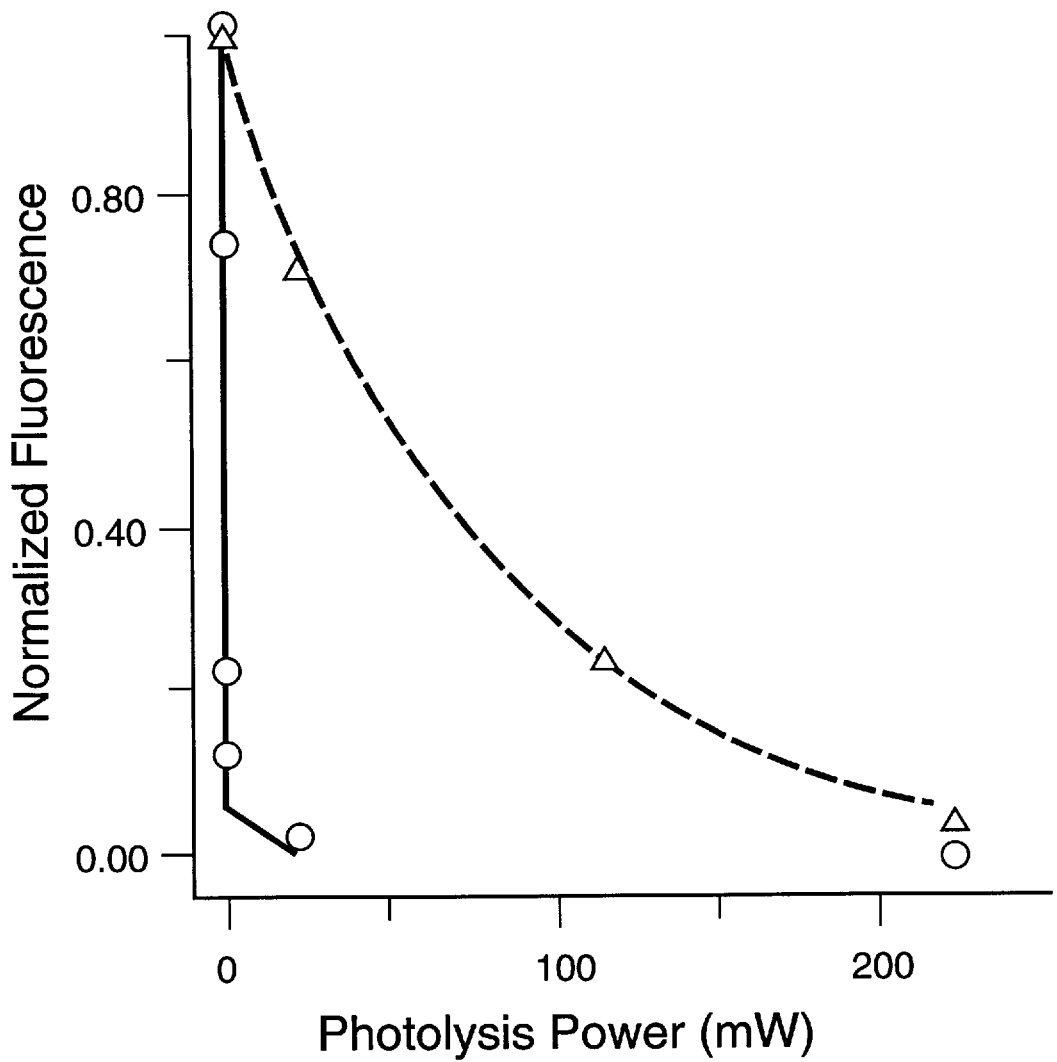
FIG. 3 graphically depicts the reduction in background fluorescence from solvents containing fluorescent molecules B-phycoerythrin and Tetramethyl-Rhodamine Isothiocyanate (TRITC).

In order to verify the effectiveness of photolysis to reduce fluorescence background in a detection region of an ultrasensitive detector, a detection system was prepared as described in P. M. Goodwin et al., "Ultrasensitive Detection of Single Molecules in Flowing Sample Streams by Laser-induced Fluorescence," 1895 SPIE, 79 (1993). Photolysis conditions were a 554 nm laser beam focused into a photolysis cell having a 0.5 mm inner diameter and 0.8 m in length. FIG. 3 illustrates the photolysis photobleaching effect on a system of B-phycoerythrin molecules (a large protein with an equivalent emission of over 20 rhodamine molecules) and a system of TRITC (a fluorescent probe molecule that is being used for single molecule detection of DNA nucleotides). The two molecules have about two orders of magnitude difference in their $\epsilon Q$ product, which allows evaluating the method over a wide range in sample properties. TRITC has a relatively low quantum yield for photodestruction ($10^{-5}$ to $10^{-6}$), which permits the method to be evaluated even when presented with extremely robust molecules. FIG. 3 shows the photolytic removal of the fluorescence of B-phycoerythrin (open circles) and TRITC (triangles) in the photolysis cell. The dashed line is the theoretical fit for TRITC and the solid line is the theoretical fit for B-phycoerythrin. The rapid removal of B-phycoerythrin fluorescence compared to TRITC is due to its higher photochemical decomposition yield and higher molar extinction coefficient compared to TRITC. The derived quantum yields, given a flow rate of 50 $\mu$L/min and $\epsilon$ at the photolysis wavelength, are about $10^{-5}$ for B-phycoerythrin and $10^{-6}$ for TRITC.

Figure 4:
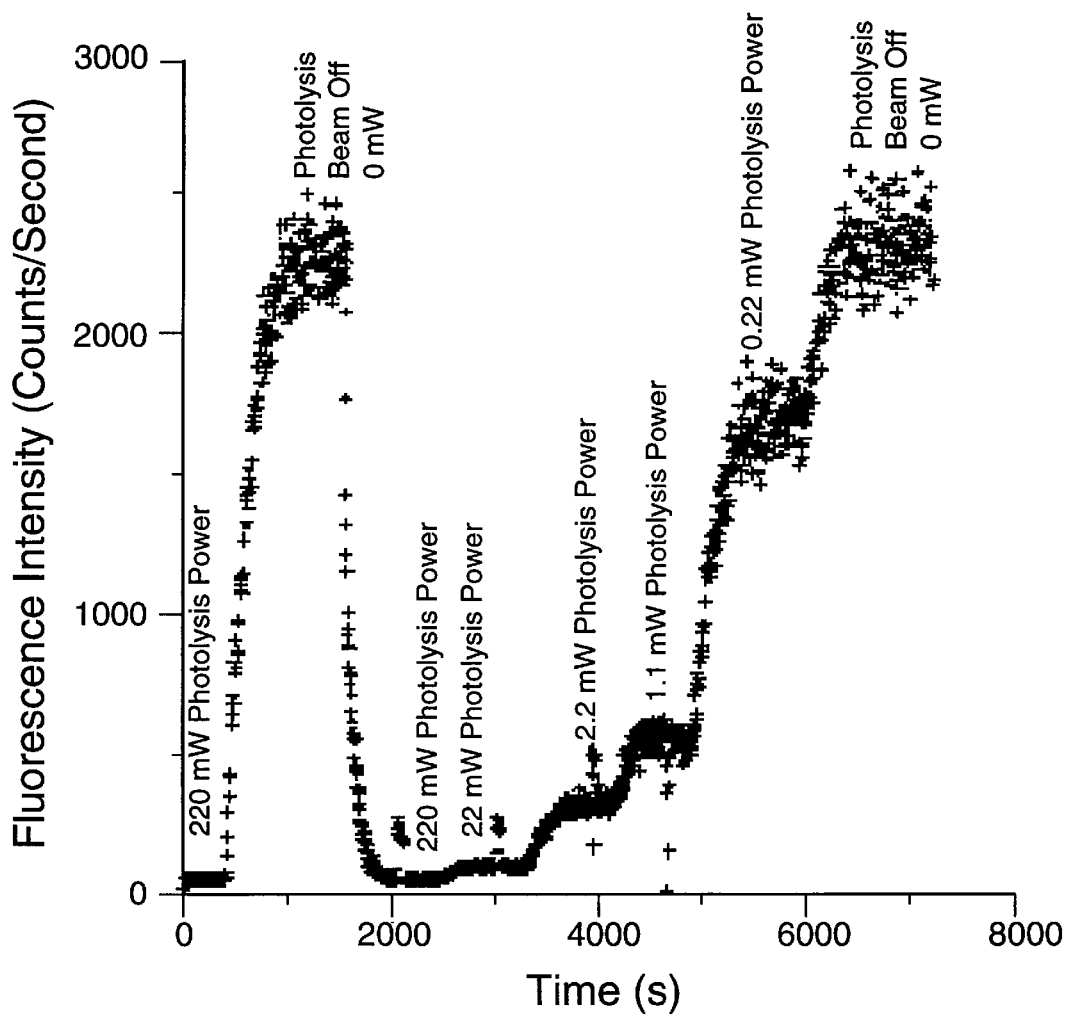
FIG. 4 graphically illustrates the effect of laser photolysis power on the fluorescence of a B-phycoerythrin flow stream.

FIG. 4 graphically shows the photolysis behavior of B-phycoerythrin at different photolysis powers in the photochemical purification cell. The B-phycoerythrin is virtually undetectable at 220 mW of photolysis power. Even at 22 and 2.2 mW of photolysis power, the photodecomposition is almost complete. The count rate is the time averaged rate of gated single photons (4 seconds). The gated count rate excludes photons arriving during and up to 2 ns after the laser pulses.

Figure 5A:
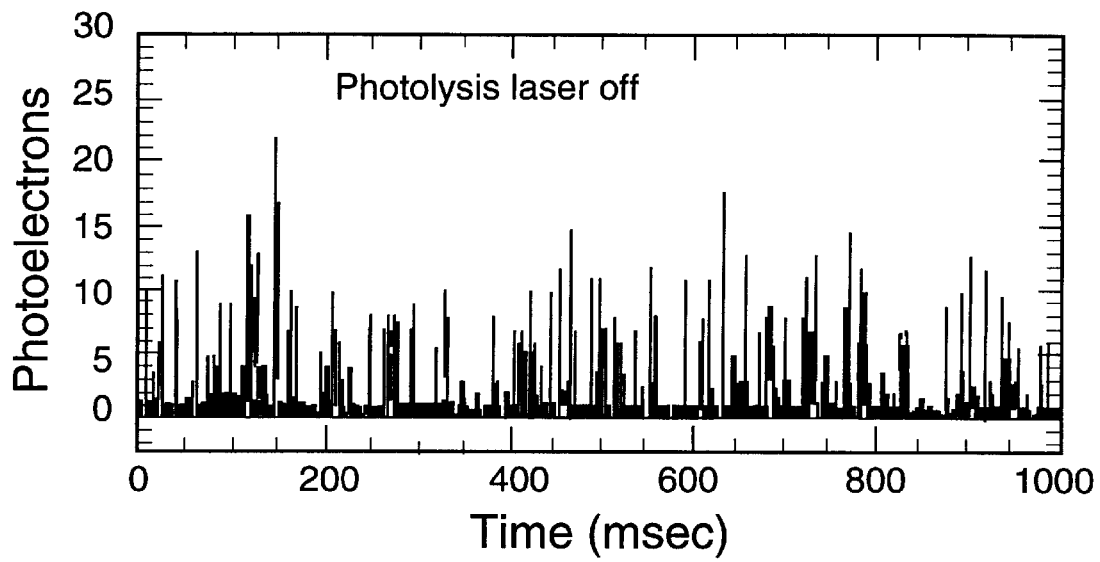
FIGS. 5A and 5B graphically illustrate the effect of photobleaching on background fluorescence from a solvent stream containing $10^{-13}$M B-phycoerythrin.
Figure 5B:
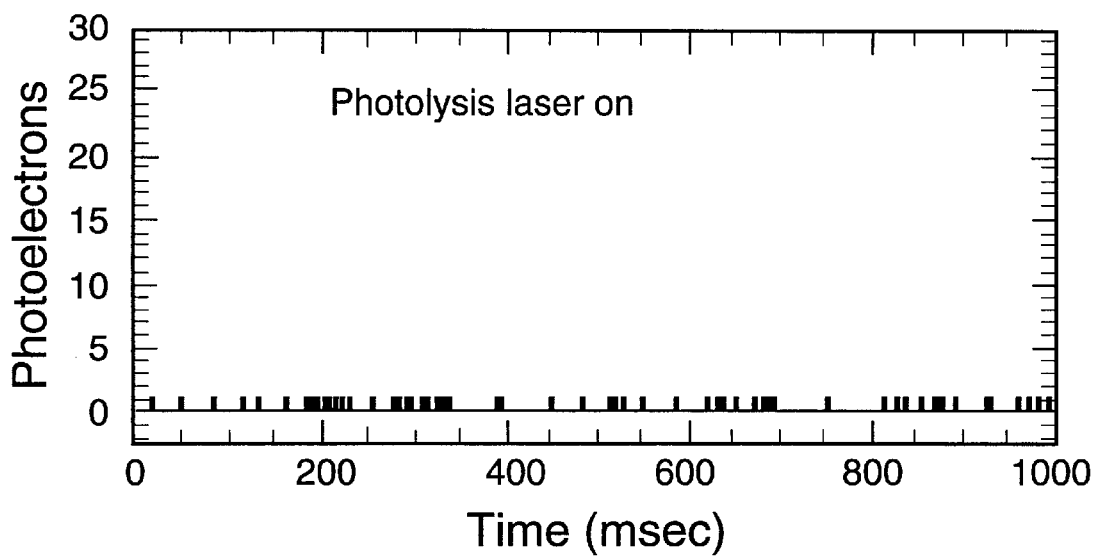

FIGS. 5A and 5B graphically depict time sequences of detected fluorescence photoelectrons from an aqueous solution of $10^{-13}$M B-phycoerythrin. FIG. 5A shows the fluorescence signal without the photolysis laser turned on. FIG. 5B shows the reduced signal due to photobleaching by the photolysis laser. Photolysis conditions were about 220 mW of laser power at 554 nm in a 0.5 mm inner diameter photolysis tube that is 0.8 m in length. Buffer flow rate was 0.05 mL/min. Photoelectrons were grouped into 0.5 millisecond bins.

Table B, below, shows the photolytic removal of background fluorescence introduced by various aqueous buffer solvent solutions that are useful in low level luminescence detection. The photolysis conditions and photon counting were identical to the conditions described for FIGS. 5A and 5B. Table B clearly shows the reduction in background luminescence as a result of photobleaching. Even highly purified water (Milli-Q water) has a reduced background as a result of photobleaching.

For a given molecule with a specific $\epsilon \phi_d$, it is the $P_0(L/V)$ that determines the efficiency of luminescence removal. Thus, it is generally desired to make this term as large as possible (i.e., high photolysis power, long path length, and low flow rate). Long path lengths, as described above, are very effective, even at relatively low photolysis powers. Because of the light-piping, even longer photolysis lengths could be employed. Adding a mirrored exterior to the photolysis cell would also enhance efficiency. A mirrored exterior would permit the photolysis beam to enter the photolysis cell at a steeper angle relative to the long axis of the tube, which would increase the path length along the tube and produce a higher effective photolysis power.

Transverse photolysis may also be used. A shorter path length is provided, so a higher average photolysis power is required. A more compact apparatus could be provided with the shorter path length. Higher peak power pulsed lasers might also be used, with a concomitant possibility of multiphoton absorptions. Multiphoton absorptions can initiate photochemistry not accessible to single photon absorptions and might be more efficient at eliminating some luminescent impurities than continuous wave photolysis.

TABLE B

Effects of Photolysis on Various Solutions

| Buffer Components | GCR Photolysis Off | GCR Photolysis On |
|---|---|---|
| Milli-Q Water | 450 | 270 |
| 10 mM Tris-HCl -diluted from 1,0 M, pH 8.0 (GIBCO-BRL) | 2200 | 580 |
| 10 mM Tris-HCl -diluted from 1.0 M, pH 8.0 (Beacon) | 1430 | 470 |
| 1X Phosphate Buffered Saline, pH 7.4 -(GIBCO-BRL) | 880 | 360 |
| 9 mM Sodium Bicarbonate -diluted from 7.5% Sodium Bicarbonate (GIBCO BRL) | 620 | 340 |
| 10 mM HEPES -diluted from 1.0 m HEPES (GIBCO-BRL) | 2640 | 570 |
| 0.05 mM Tris-HCl -diluted from 1.0 M, pH 8.0 (Beacon) 5 mM MgCl$_2$ -diluted from 0.1 M (Beacon) 300 Units/mL Exonuclease III -diluted from 100,000 Units/mL (New England Biolabs | 2120 | 710 |

For the photolysis results presented above, the photolysis beam wavelength was the same as the wavelength used to excite the fluorophore. Identical wavelengths were selected for experimental convenience and to generally ensure that fluorescent impurities were being decomposed at the same wavelength as that used to excite the sample. However, other photolysis wavelengths may be selected for analytical purposes.

Generally, the material to be photobleached must absorb a photon so that the photon wavelength must fall in an absorption band of the material to be photolyzed. Emissions generally arise from the lowest singlet or triplet state of a molecule so that the emission of an interferent will almost always fall to the red of its lowest energy absorptions. Therefore, in most cases the photolysis beam should be to the blue of the luminescence wavelength being monitored for the analyte. While photolysis to the red of the analyte emission might eliminate impurities, these impurities would usually be materials that emit at a wavelength that is too long to interfere with analyte luminescence.

Using another wavelength permits use of another laser or type of laser other than the analysis laser. Another laser may have more available power than the analysis laser. For example, a Ar$^+$ laser pumped mode-locked dye laser used to obtain the data herein described is limited to about 250 mW of photolysis power. By using another cw Ar$^+$ laser operating on all lines, many watts of photolysis power are possible. An increase in $P_0$ increases the efficiency of photodestruction.

It is well known that many molecules absorb more intensely as shorter wavelengths are used. Thus, using a shorter wavelength photolysis beam could increase $\epsilon$. Because of the exponential dependence of the photolysis equation, even a modest increase in $\epsilon$ could dramatically increase the efficiency of photochemical destruction of interferents. This would also be true if one were exciting on the long wavelength edge of the emitting state of the interferent. A relatively small blue shift in photolysis wavelength would move up the absorption band to the peak of the lowest energy absorption and dramatically improve photolysis efficiency.

Finally, it is not uncommon for photochemistry or the probability for molecular photodestruction, $\epsilon_d$, to increase in efficiency as the photon energy increase (i.e., shorter wavelengths). This is a result of excitation of different types of excited states that only absorb at higher energy and the higher energy per photon being deposited into the molecule.

In some applications, it is desirable to contact the sample with an active agent, e.g., an exonuclease to cleave a DNA strand at one or more locations. The activity of one common enzyme, exonuclease III (ExoIII), was investigated under a variety of conditions:

1. photolyzed buffer; fresh enzyme;
2. buffer and enzyme solution, both photolyzed;
3. buffer and enzyme solution, not photolyzed.

The enzyme activity was determined by digesting a linearized pUC19 vector and doing a gel analysis on the resulting DNA fragments. The analysis showed that enzyme activity was not affected either by application in a photolyzed buffer or by being photolyzed.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for reducing solvent luminescence background emissions in a detection system for a sample that becomes luminescent when excited by light at an exciting wavelength, comprising the steps of:

illuminating said solvent with said sample with a first light in a first region of said detection system effective to form a photobleached solvent;

introducing said photobleached solvent and said sample into a second region of said detection system downstream of said first region, where said first light is absent from said second region; and illuminating said photobleached solvent and said sample with a second light having said exciting wavelength to luminesce said sample in said second region.

2. A method according to claim 1, wherein said sample is nucleotides from a DNA strand tagged with fluorescent molecules.

3. A method according to claim 2, wherein said solvent in said first region includes an enzyme effective to cleave said nucleotides from said DNA strand and said first light has a wavelength effective to photobleach interferants in said solvent while said enzyme remains effective to cleave said DNA strand.

4. A method according to claim 2, wherein an enzyme is introduced into said second region to cleave said nucleotides from said DNA strand.

5. A method according to claim 1, wherein said first and second lights have the same wavelength.

6. A method according to claim 5, wherein said sample is nucleotides from a DNA strand tagged with fluorescent molecules.

7. A method according to claim 6, wherein said solvent in said first region includes an enzyme effective to cleave said nucleotides from said DNA strand and said first light has a wavelength effective to photobleach interferants in said solvent while said enzyme remains effective to cleave said DNA strand.

8. A method for reducing solvent luminescence background emissions in a detection system for a sample that becomes luminescent when excited by light at an exciting wavelength, comprising the steps of:

illuminating said solvent with said sample with a first light in a first region of said detection system effective to form a photobleached solvent;

introducing said sample into said photobleached solvent in a second region of said detection system downstream of said first region, where said first light is absent from said second region; and illuminating said photobleached solvent and said sample with a second light having said exciting wavelength to luminesce said sample in said second region.

9. A method according to claim 8, wherein said sample is nucleotides from a DNA strand tagged with fluorescent molecules.

10. A method according to claim 9, wherein said solvent in said first region includes an enzyme effective to cleave said nucleotides from said DNA strand and said first light has a wavelength effective to photobleach interferants in said solvent while said enzyme remains effective to cleave said DNA strand.

11. A method according to claim 9, wherein an enzyme is introduced into said second region to cleave said nucleotides from said DNA strand.

12. A method according to claim 8, wherein said first and second lights have the same wavelength.

13. A method according to claim 12, wherein said sample is nucleotides from a DNA strand tagged with fluorescent molecules.

14. A method according to claim 13, wherein said solvent in said first region includes an enzyme effective to cleave said nucleotides from said DNA strand and said first light has a wavelength effective to photobleach interferants in said solvent while said enzyme remains effective to cleave said DNA strand.

* * * * *